US007476382B2

(12) United States Patent
Lee et al.

(10) Patent No.: US 7,476,382 B2
(45) Date of Patent: *Jan. 13, 2009

(54) REOVIRUS FOR THE TREATMENT OF NEOPLASIA

(75) Inventors: Patrick W. K. Lee, Calgary (CA); James Strong, Calgary (CA); Matthew C. Coffey, Calgary (CA)

(73) Assignee: Oncolytics Biotech Inc. (CA)

( * ) Notice: Subject to any disclaimer, the term of this patent is extended or adjusted under 35 U.S.C. 154(b) by 471 days.

This patent is subject to a terminal disclaimer.

(21) Appl. No.: 10/836,857

(22) Filed: Apr. 30, 2004

(65) Prior Publication Data

US 2005/0123513 A1    Jun. 9, 2005

Related U.S. Application Data

(63) Continuation of application No. 09/989,101, filed on Nov. 21, 2001, now abandoned, which is a continuation of application No. 09/569,865, filed on May 12, 2000, now Pat. No. 6,344,195, which is a continuation of application No. 08/911,383, filed on Aug. 13, 1997, now Pat. No. 6,110,461.

(51) Int. Cl.
*A61K 48/00* (2006.01)
*C12N 7/01* (2006.01)
*C12Q 1/68* (2006.01)
*C12Q 1/70* (2006.01)

(52) U.S. Cl. .................. 424/93.2; 424/93.1; 424/93.6; 435/235.1

(58) Field of Classification Search ...................... None
See application file for complete search history.

(56) References Cited

U.S. PATENT DOCUMENTS

| 4,108,983 | A | | 8/1978 | Wallack |
| 4,205,131 | A | | 5/1980 | Almeida |
| 4,490,358 | A | * | 12/1984 | Greene et al. ............ 424/131.1 |
| 5,525,342 | A | | 6/1996 | Rosenberger et al. |
| 6,110,461 | A | | 8/2000 | Lee et al. |
| 6,136,307 | A | | 10/2000 | Lee et al. |
| 6,261,555 | B1 | | 7/2001 | Lee et al. |
| 6,344,195 | B1 | | 2/2002 | Lee et al. |

FOREIGN PATENT DOCUMENTS

| EP | 0453242 A1 | 10/1991 |
| EP | 0514603 A1 | 11/1992 |
| WO | 90/09441 | 8/1990 |
| WO | 90/11765 | 10/1990 |
| WO | 94/18992 | 9/1994 |
| WO | 97/04805 | 2/1997 |
| WO | 97/16443 | 5/1997 |
| WO | 98/08541 | 3/1998 |
| WO | 99/08692 | 2/1999 |
| WO | 99/18799 | 4/1999 |

OTHER PUBLICATIONS

Sherry et al. The reovirus M1 gene, encoding a viral core protein, is associated with the myocarditic phenotype of a reovirus variant. Journal of Virology (1989) vol. 63 (11), pp. 4850-4856.*
Flamand et al., J. Virol., 1991, vol. 65, No. 1, pp. 123-131.*
G. Hashiro et al., "The Preferential Cytotoxicity of Reovirus for Certain Transformed Cell Lines", *Archives of Virology* 54(4):307-315 (1977).
J.E. Strong et al., "The Molecular Basis of Viral Oncolysis: Usurption of the Ras Signaling Pathway by Reovirus", *The EMOB Journal* 17(12):3351-3362 (Jun. 15, 1998).
Tang et al., "Short Communications: Recognition of the Epidermal Growth Factor Receptor by Reovirus", *Virology* 197:412-414 (1993).
Sharp et al., "Homologous regions of the α subunit of eukaryotic translational initiation factor 2 (eIF2α) and the vaccinia virus K3L gene product interact with the same domain within the dsRNA-activated protein kinase (PKR)" *Eur. J. Biochem.* 250:85-91 (1997).
Randazzo et al., "Herpes simplex virus 1716, and ICP 34.5 null mutant, is unable to replicate in CV-1 cells due to a translational block that can be overcome by coinfection with SV40" *J. of Gen. Virol.* 78:3333-3339 (1997).
He et al., "Suppression of the Phenotype of .γ₁ 34.5-Herpes Simplex Virus 1: Failure of Activated RNA-Dependent Protein Kinase to Shut Off Protein Synthesis is Associated with a Deletion in the Domain of the α47 Gene" *J. Virol.* 71(8):6049-6054 (Aug. 1997).
Gale, Jr. et al., "Evidence that Hepatitis C Virus Resistance to Interferon is Mediated Through Repression of the PKR Protein Kinase by the Nonstructural 5A Protein" *Virology* 230:217-227 (1997).
Kawagishi-Kobayashi et al., "Regulation of the Protein Kinase PKR by the Vaccinia Virus Pseudosubstrate Inhibitor K3L is Dependent on Residues Conserved Between the K3L Protein and the PKR Substrate 3IF2α" *Mol. and Cell Biol.* 17(7):4146-4158 (1997).
Steele, T.A. and Cox, D.C., "Reovirus Type 3 Chemoimmunotherapy of Murine Lymphoma is Abrogated by Cyclosporine," *Cancer Biotherapy*, 10(4): 307-315 (1995).
Cahill, M.A., et al., "Signalling pathways: Jack of all cascades," *Current Biology*, 6(1):16-19 (1996).
Macara, I.G., et al, "The Ras superfamily of GTPases," *The FASEB Journal*, 10:625-630 (1996).

(Continued)

*Primary Examiner*—David Guzo
(74) *Attorney, Agent, or Firm*—Fish & Richardson P.C.

(57) ABSTRACT

Methods for treating neoplasia, by administering reovirus to a Ras-mediated neoplasm, are disclosed. The reovirus is administered so that it ultimately directly contacts cells of the neoplasm. Human reovirus, non-human mammalian reovirus, and/or avian reovirus can be used. If the reovirus is human reovirus, type 1 (e.g., strain Lang), type 2 (e.g., strain Jones), type 3 (e.g., strain Dearing or strain Abney), as well as other serotypes or strains of reovirus can be used. Combinations of more than one type and/or strain of reovirus can be used, as can reovirus from different species of animal. Either solid neoplasms or hematopoietic neoplasms can be treated.

23 Claims, 1 Drawing Sheet

OTHER PUBLICATIONS

Marshall, C.J., "Ras effectors," *Current Opinion in Cell Biology*, 8:197-204 (1996).

Strong, J.E. and Lee, P.W.K., "The v-*erbB* Oncogene Confers Enhanced Cellular Susceptibility to Reovirus Infection," *J. of Virol.* 70(1):612-616 (1996).

Strong, J.E. et al., "Evidence That the Epidermal Growth Factor Receptor on Host Cells Confers Reovirus Infection Efficiency," *Virol.* 197:405-411. (1993).

Duncan, M.R. et al., "Differential Sensitivity of Normal and Transformed Human Cells to Reovirus Infection," *J. of Virol.* 28(2):444-449 (1978).

Soroceanu, L. et al., "The Use of Genetically Engineered HSV-1 Viruses in Treatment of Malignant Intracerebral Gliomas," *FASEB.J.* 9(3): Abstract 812 p. A139 (1995).

Andreansky, S.S. et al., "The application of genetically engineered herpes simplex viruses to the treatment of experimental brain tumors," *Proc. Natl. Acad. Sci.* USA 93:11313-11318 (1996).

Boviatsis, E.J. et al., "Antitumor activity and reporter gene transfer into rat brain neoplasms inoculated with herpes simplex virus vectors defective in thymidine kinase or ribonucleotide reductase," *Gene Therapy* 1:323-331 (1994).

Taterka, J. et al., "Characterization of Cytotoxic Cells from Reovirus-Infected SCID Mice: Activated Cells Express Natural Killer-and Lymphokine-Activated Killer-Like Acitvity but Fail To Clear Infection," *J. of Virol.* 69 (6):3910-3914 (1995).

Zhang, J.F. et al., "Treatment of a human breast cancer xenograft with an adenovirus vector containing an interferon gene results in rapid regression due to viral oncolysis and gene therapy," *Proc. Natl. Acad. Sci.* USA 93:4513-4518 (1996).

Chambers, R. et al., "Comparison of genetically engineered herpes simplex viruses for the treatment of brain tumors in a *scid* mouse model of human malignant glioma," *Proc. Natl. Acad. Sci. USA* 92:1411-1415 (1995).

Williams, M.E. et al., "Rejection of reovirus-treated L1210 leukemia cells by mice," *Cancer Immunol. Immunother.* 23:87-92 (1986).

Theiss, J.C. et al., "Effect of Reovirus Infection on Pulmonary Tumor Response to Urethan in Strain A Mice," *J. Natl Cancer Inst* 61:131-134 (1978).

Kollmorgen, G.M. et al., "Immunotherapy of EL4 Lymphoma with Reovirus," *Cancer Immunol. Immunother.* 1:239-244 (1976).

Bryson, J.S. and Cox, D.C., "Characteristics of reovirus-mediated chemoimmunotherapy of murine L1210 leukemia," *Cancer Immunol. Immunother.* 26: 132-138 (1988).

Gentsch, J.R. and Pacitti, A.F., "Effect of Neuraminidase Treatment of Cells and Effect of Soluble Glycoproteins on Type 3 Reovirus Attachment to Murine L Cells," *J. of Virol.* 56 (2):356-364 (1985).

Armstrong, G.D. et al., "Studies on Reovirus Receptors of L Cells: Virus Binding Characteristics and Comparison with Reovirus Receptors of Erythrocytes," *Virology* 138:37-48 (1984).

Samuel, C.E. and Brody, M.S., "Biosynthesis of Reovirus-Specified Polypeptides—2-Aminopurine Increases the Efficiency of Translation of Reovirus s1 mRNA but not 54 mRNA in Transfected Cells," *Virology* 176:106-113 (1990).

Mundschau, L.J. and Faller, D.V., "Oncogenic *ras* Induces an Inhibitor of Double-stranded RNA-dependent Eukaryotic Initiation Factor 2α-kinase Activation," *The J. of Biol. Chem.* 267 (32):23092-23098 (1992).

Avruch, J. et al., "Raf meets Ras: completing the framework of a signal transduction pathway," *Trends Bioch. Sci.* 19:279 (1994).

Barbacid, M., "*ras* Genes," *Annu. Rev. Biochem.* 56:779-827 (1987).

Hershey, J.W.B., "Translation Control on Mammalian Cells," *Annu. Rev. Biochem.* 60:717-755 (1991).

Jon R. Gentsch et al., Genetic Diversity in Natural Populations of Mammalian Reoviruses: Tryptic Peptide Analysis of Outer Capsid Polypeptides of Murine, Bovine, and Human Type 1 and 3 Reovirus Strains, *Journal of Virology* Mar. 1984, pp. 641-651.

Coffey, Matthew C. et al., "Reovirus Therapy of Tumors with Activated Ras Pathway," *Science* (Washington D.C.), vol. 282, No. 5392 Nov. 13, 1998, pp. 1332-1334.

Chandran, Kartik et al., "Protease Cleavage of Reovirus Capsid Protein μl/μlC is Blocked by Alkyl Sulfate Detergents, Yielding a New Type of Infectious Subvirion Particle," *Journal of Virology*, vol. 72, No. 1, Jan. 1988 pp. 467-475.

Hall-Jackson, C.A. et al., "Induction of Cell Death by Stimulation of Protein Kinase C in Human Epithelial Cells Expressing a Mutant *ras* Oncogene: A Potential Therapeutic Target," *British Journal of Cancer*, vol. 78, No. 5, 1998, pp. 641-651.

Database Biosis Online!, Biosciences Information Service, Philadelphia, PA, US; 1996, Bollag Gideon et al., "Loss of NF1 Results in Activation of the Ras Signalling Pathway and Leads to Aberrant Growth in Haematopoietic Cells," *Nature Genetics*, vol. 12, No. 2, 1996, pp. 144-148.

Aronheim, A. et al., "Membrane Targeting of the Nucleotide Exchange Factor Sos is Sufficient for Activating the Ras Signaling Pathway", *Cell*, 78:949-961, (1994).

Berrozpe, G. et al., "Comparative Analysis of Mutations in the *p53* and K-*ras* Genes in Pancreatic Cancer," *Int. J. Cancer*, 58:185-191 (1994).

Bischoff, J. et al., "Mechanism of Interferon Action; Activation of the Human P1/eIF-2α Protein Kinase by Individual Reovirus s-Class mRNAs: s1 mRNA is a Potent Activator Relative to s4 mRNA", *Virology*, 172:06-115 (1989).

Bos, J. L., "*ras* Oncogenes in Human Cancer: A Review", *Cancer Research*, 49:4682-4689, (1989).

Chaubert, P. et al. "K-*ras* Mutations and p53 Alterations in Neoplastic and Nonneoplastic Lesions Associated with Logstanding Ulcerative Colitis", *American Journal of Pathology*, vol. 144, No. 4:767-775 (1994).

Der, S. et al., "A double-stranded RNA-activated protein kinase-dependent pathway mediating stress-induced apoptosis", *Proc. Natl. Acad. Sci. USA*, 94:3279-3283 (1997).

Dudley, D. et al., A synthetic inhibitor of the mitogen-activated protein kinase cascade, *Proc. Natl. Acad. Sci. USA*, 92:7686-7689 (1995).

Helbing, C. et al., "A Novel Candidate Tumor Suppressor, *ING1*, is Involved in the Regulation of Apoptosis", *Cancer Research*, 57:1255-1258 (1997).

Hu, Y et al., "2-Aminopurine Inhibits the Double-Stranded RNA-Dependent Protein Kinase Both In Vitro and In Vivo", *Journal of Interferon Research*, 13:323-328 (1993).

Jackson, G. G. et al., "Viruses Causing Common Respiratory Infection in Man. IV.Reoviruses and Adenoviruses", *The Journal of Infectious Diseases*, 128(6): 811-866 (1973).

Janes, Peter W. et al., "Activation of the Ras signalling pathway in human breast cancer cells overexpressing *erb*B-2", *Oncogene* 9:3601-3608 (1994).

Laemmli, U. K. "Cleavage of Structural Proteins During the Assembly of the Head of Bacteriophage T4", *Nature*, 227:680-685 (1970).

Lee, Jonathan M. et al. "p53 mutations increase resistance to ionizing radiation", *Proc. Natl. Acad. Sci. USA*, 90:5742-5746 (1993).

Lee, P. W. K. et al., "Characterization of Anti-Reovirus Immunoglobulins Secreted by Cloned Hybridoma Cell Lines", *Virology* 108:134-146 (1981).

Levitzki, Alexander, "Signal-transduction therapy a novel approach to disease management", *Eur. J. Biochem.* 226:1-13 (1994).

Lowe, Scott W. et al., "p53 Status and the Efficacy of Cancer Therapy in Vivo", *Science*, 226:807-810 (1994).

McCrae, Malcolm A. et al., "The Nature of the Polypeptide Encoded by Each of the 10 Double-Stranded RNA Segments of Reovirus Type 3", *Virology*, 89:578-593 (1978).

Mills, Nancy E. et al. "Increased Prevalence of K-*ras* Oncogene Mutations in Lung Adenocarcinoma", *Cancer Research*, 55:1444-1447 (1995).

Nagata, Les et al., "Molecular cloning and sequencing of the reovirus (serotype 3) S1 gene which encodes the viral cell attachment protein σ1", *Nucleic Acids Research*, 12:8699-8710 (1984).

Paul, Ralph W. et al. "The α-Anomeric Form Sialic is the Minimal Receptor Determinant Recognized by Reovirus", *Virology*, 172:382-385 (1989).

Raybaud-Diogène, et al., "Markers of Radioresistance in Squamous Cell Carcinomas of the Head and Neck: A Clinicopathologic and Immunohistochemical Study", *Journal of Clinical Oncology*, 15(3):1030-1038 (1997).

Robinson, Megan J. et al., "Mitogen-activated protein kinase pathways", *Current Opinion in Cell Biology*, 9:180-186 (1997).

Rosen, Leon, "Serologic Grouping of Reoviruses by Hemagglutination-Inhibition", *Am. J. Hyg.* 71:242-249 (1960).

Sabin, A. B. "Science in the News", *Science*, 130:966-972 (1959).

Smith R. E., et al., "Polypeptide Components of Virions, Top Component and Cores of Reovirus Type 3", *Virology*, 39:791-810 (1969).

Stanley, N. F., "Reoviruses", *Br. Med. Bull.*, 150-154 (1967).

Trimble, W. S., et al., "Inducible cellular transformation by a metallothionein-*ras* hybrid onocogene leads to natural killer cell susceptibility", *Nature*, 321:782-784 (1986).

Tyler, Kenneth L. et al., "Reoviruses", *Fields Virology, Third Edition*, Lippencott-Raven, Philadelphia pp. 1597-1623 (1996).

Waters, Steven B. et al., "Desensitization of Ras Activation by a Feedback Disassociation of the SOS-Grb2 Complex", *Journal of Biological Chemistry*, 270(36):20883-20886 (1995).

Wiesmüller, Lisa et al., "Signal Transduction Pathways Involving Ras Mini Review", *Cellular Signalling*, 6(3):247-267 (1994).

Wong, Howard, et al., "Monitoring mRNA Expression by Polymerase Chain Reaction: The 'Primer-Dropping' Method", *Analytical Biochemistry*, 223:251-258 (1994).

Yang, Yi-Li et al., "Deficient signalling in mice devoid of double stranded RNA-dependent protein kinase", *The Embo Journal*, 14(24):6095-6106 (1995).

Yu, Dihua, et al., "Overexpression of c-*erb*B-2/*neu* in breast cancer cells confers increased resistance to Taxol via *mdr-1*-Independent Mechanisms", *Oncogene*, 13:1359-1365 (1996).

\* cited by examiner

REOVIRUS FOR THE TREATMENT OF NEOPLASIA

CROSS-REFERENCE TO RELATED APPLICATIONS

This application is a continuation application of U.S. application Ser. No. 09/989,101, filed on Nov. 21, 2001, now abandoned which is continuation application of U.S. application Ser. No. 09/569,865, filed on May 12, 2000, now U.S. Pat. No. 6,344,195, which is a continuation of U.S. application Ser. No. 08/911,383, filed on Aug. 13, 1997, now U.S. Pat. No. 6,110,461. Each of these prior applications is herein incorporated by reference in its entirety.

BACKGROUND OF THE INVENTION

Normal cell proliferation is regulated by a balance between growth-promoting proto-oncogenes and growth-constraining tumor-suppressor genes. Tumorigenesis can be caused by genetic alterations to the genome that result in the mutation of those cellular elements that govern the interpretation of cellular signals, such as potentiation of proto-oncogene activity or inactivation of tumor suppression. It is believed that the interpretation of these signals ultimately influences the growth and differentiation of a cell, and that misinterpretation of these signals can result in neoplastic growth (neoplasia).

Genetic alteration of the proto-oncogene Ras is believed to contribute to approximately 30% of all human tumors (Wiessmuller, L. and Wittinghofer, F. (1994), *Cellular Signaling* 6(3):247-267; Barbacid, M. (1987) *A Rev. Biochem.* 56, 779-827). The role that Ras plays in the pathogenesis of human tumors is specific to the type of tumor. Activating mutations in Ras itself are found in most types of human malignancies, and are highly represented in pancreatic cancer (80%), sporadic colorectal carcinomas (40-50%), human lung adenocarcinomas (15-24%), thyroid tumors (50%) and myeloid Leukemia (30%) (Millis, N E et al. (1995) *Cancer Res.* 55:1444; Chaubert, P. et al. (1994), *Am. J. Path.* 144:767; Bos, J. (1989) *Cancer Res.* 49:4682). Ras activation is also demonstrated by upstream mitogenic signaling elements, notably by tyrosine receptor kinases (RTKs). These upstream elements, if amplified or overexpressed, ultimately result in elevated Ras activity by the signal transduction activity of Ras. Examples of this include overexpression of PDGFR in certain forms of glioblastomas, as well as in c-erbB-2/neu in breast cancer (Levitzki, A. (1994) *Eur. J. Biochem.* 226:1; James, P. W., et al. (1994) *Oncogene* 9:3601; Bos, J. (1989) *Cancer Res.* 49:4682).

Current methods of treatment for neoplasia include surgery, chemotherapy and radiation. Surgery is typically used as the primary treatment for early stages of cancer; however, many tumors cannot be completely removed by surgical means. In addition, metastatic growth of neoplasms may prevent complete cure of cancer by surgery. Chemotherapy involves administration of compounds having antitumor activity, such as alkylating agents, antimetabolites, and antitumor antibiotics. The efficacy of chemotherapy is often limited by severe side effects, including nausea and vomiting, bone marrow depression, renal damage, and central nervous system depression. Radiation therapy relies on the greater ability of normal cells, in contrast with neoplastic cells, to repair themselves after treatment with radiation. Radiotherapy cannot be used to treat many neoplasms, however, because of the sensitivity of tissue surrounding the tumor. In addition, certain tumors have demonstrated resistance to radiotherapy and such may be dependent on oncogene or anti-oncogene status of the cell (Lee. J. M. et al. (1993) *PNAS* 90:5742-5746; Lowe. S. W. et al. (1994) *Science,* 266:807-810; Raybaud-Diogene. H. et al. (1997) *J. Clin. Oncology,* 15(3):1030-1038). In view of the drawbacks associated with the current means for treating neoplastic growth, the need still exists for improved methods for the treatment of most types of cancers.

SUMMARY OF THE INVENTION

The present invention pertains to methods for treating neoplasia in a mammal, using reovirus. Reovirus is administered to a neoplasm, in which an element of the Ras signaling pathway (either upstream or downstream) is activated to an extent that results in reovirus-mediated oncolysis of cells of the neoplasm. The reovirus can be administered in a single dose or in multiple doses; furthermore, more than one neoplasm in an individual mammal can be treated concurrently. Both solid neoplasms and hematopoietic neoplasms can be targeted. The reovirus is administered so that it contacts cells of the mammal (e.g., by injection directly into a solid neoplasm, or intravenously into the mammal for a hematopoietic neoplasm). The methods can be used to treat neoplasia in a variety of mammals, including mice, dogs, cats, sheep, goats, cows, horses, pigs, and non-human primates. Preferably, the methods are used to treat neoplasia in humans.

The methods of the invention provide an effective means to treat neoplasia, without the side effects associated with other forms of cancer therapy. Furthermore, because reovirus is not known to be associated with disease, any safety concerns associated with deliberate administration of a virus are minimized.

DETAILED DESCRIPTION OF THE INVENTION

Figure 1:
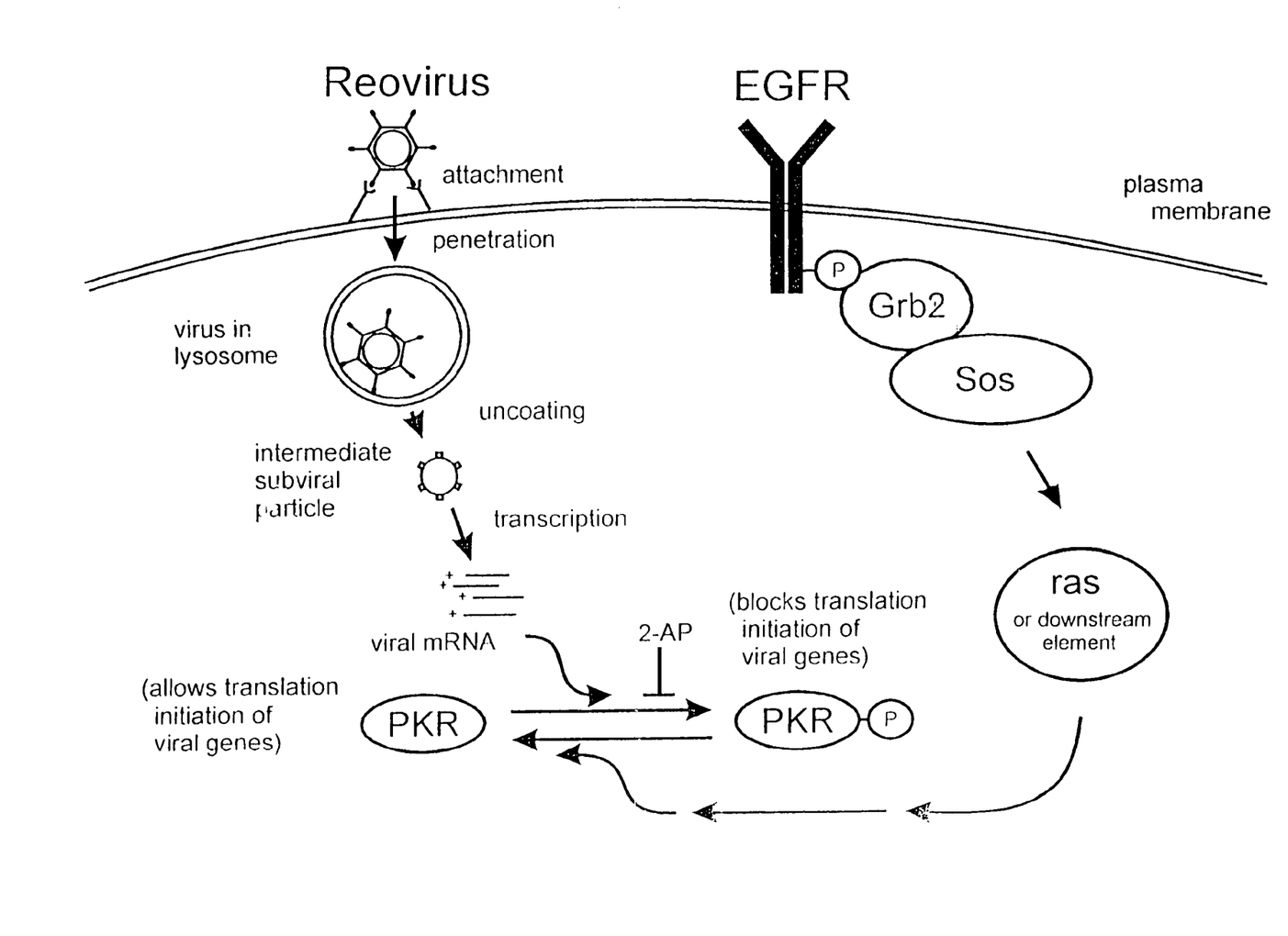
The FIGURE is a depiction of the molecular basis of reovirus oncolysis, in which the reovirus usurps the host cell Ras signalling pathway.

The invention pertains to methods of treating a neoplasm in a mammal, by administering reovirus to the neoplasm. The name reovirus (Respiratory and enteric orphan virus) is a descriptive acronym suggesting that these viruses, although not associated with any known disease state in humans, can be isolated from both the respiratory and enteric tracts (Sabin, A. B. (1959), *Science* 130:966). The mammalian reovirus consists of three serotypes: type 1 (strain Lang or T1L), type 2 (strain Jones, T2J) and type 3 (strain Dearing or strain Abney, T3D). The three serotypes are easily identifiable on the basis of neutralization and hemagglutinin-inhibition assays (Sabin, A. B. (1959), *Science* 130:966; Fields, B. N. et al. (1996), *Fundamental Virology* 3rd Edition, Lippincott-Raven; Rosen, L. (1960) *Am. J. Hyg.* 71:242; Stanley, N. F. (1967) *Br. Med. Bull.* 23:150).

Although reovirus is not known to be associated with any particular disease, many people have been exposed to reovirus by the time they reach adulthood (i.e., fewer than 25% in children<5 years old, to greater than 50% in those 20-30 years old (Jackson G. G. and Muldoon R. L. (1973) *J. Infect. Dis.* 128:811; Stanley N. F. (1974) *In: Comparative Diagnosis of Viral Diseases,* edited by E. Kurstak and K. Kurstak, 385-421, Academic Press, New York).

For mammalian reoviruses, the cell surface recognition signal is sialic acid (Armstrong, G. D. et al. (1984), *virology* 138:37; Gentsch, J. R. K. and Paciti, A. F. (1985), *J. Virol.*

56:356; Paul R. W. et al. (1989) *Virology* 172:382-385). Due to the ubiquitous nature of sialic acid, reovirus binds efficiently to a multitude of cell lines and as such can potentially target many different tissues; however, there are significant differences in susceptibility to reovirus infection between cell lines.

As described herein, Applicants have discovered that cells which are resistant to reovirus infection became susceptible to reovirus infection when transformed with a gene in the Ras pathway. "Resistance" of cells to reovirus infection indicates that infection of the cells with the virus did not result in significant viral production or yield. Cells that are "susceptible" are those that demonstrate induction of cytopathic effects, viral protein synthesis, and/or virus production. Resistance to reovirus infection was found to be at the level of gene translation, rather than at early transcription: while viral transcripts were produced, virus proteins were not expressed. Viral gene transcription in resistant cells correlated with phosphorylation of an approximately 65 kDa cell protein, determined to be double-stranded RNA-activated protein kinase (PKR), that was not observed in transformed cells. Phosphorylation of PKR lead to inhibition of translation. When phosphorylation was suppressed by 2-aminopurine, a known inhibitor of PKR, drastic enhancement of reovirus protein synthesis occurred in the untransformed cells. Furthermore, in a severe combined immunodeficiency (SCID) mouse model in which tumors were created on both the right and left hind flanks revealed that reovirus significantly reduced tumor size when injected directly into the right-side tumor; in addition, significant reduction in tumor size was also noted on the left-side tumor which was not directly injected with reovirus, indicating that the oncolytic capacity of the reovirus was systemic as well as local.

These results indicated that reovirus uses the host cell's Ras pathway machinery to downregulate PKR and thus reproduce. The FIGURE depicts the usurpation of the host cell Ras signalling pathway by reovirus. As shown in the FIGURE, for both untransformed (reovirus-resistant) and EGFR-, Sos-, or ras-transformed (reovirus-susceptible) cells, virus binding, internalization, uncoating, and early transcription of viral genes all proceed normally. In the case of untransformed cells, secondary structures on the early viral transcripts inevitably trigger the phosphorylation of PKR, thereby activating it, leading to the phosphorylation of the translation initiation factor eIF-2α, and hence the inhibition of viral gene translation. In the case of EGFR-, Sos-, or ras-transformed cells, the PKR phosphorylation step is prevented or reversed by Ras or one of its downstream elements, thereby allowing viral gene translation to ensue. The action of Ras (or a downstream element) can be mimicked by the use of 2-aminopurine (2-AP), which promotes viral gene translation (and hence reovirus infection) in untransformed cells by blocking PKR phosphorylation.

Based upon these discoveries, Applicants have developed methods for treating neoplasms in mammals. Representative mammals include mice, dogs, cats, sheep, goats, cows, horses, pigs, non-human primates, and humans. In a preferred embodiment, the mammal is a human.

In the methods of the invention, reovirus is administered to a neoplasm in the individual mammal. Representative types of human reovirus that can be used include type 1 (e.g., strain Lang or T1L); type 2 (e.g., strain Jones or T2J); and type 3 (e.g., strain Dearing or strain Abney, T3D or T3A); other strains of reovirus can also be used. In a preferred embodiment, the reovirus is strain Dearing. Alternatively, the reovirus can be a non-human mammalian reovirus (e.g., non-human primate reovirus, such as baboon reovirus; equine; or canine reovirus), or a non-mammalian reovirus (e.g., avian reovirus). A combination of different serotypes and/or different strain of reovirus, such as reovirus from different species of animal; can be used. The reovirus is "naturally-occurring": that is, it can be isolated from a source in nature and has not been intentionally modified by humans in the laboratory. For example, the reovirus can be from a "field source": that is, from a human patient. If desired, the reovirus can be chemically or biochemically pretreated (e.g., by treatment with a protease, such as chymotrypsin or trypsin) prior to administration to the neoplasm. Such pretreatment removes the outer coat of the virus and may thereby result in better infectivity of the virus.

The neoplasm can be a solid neoplasm (e.g., sarcoma or carcinoma), or a cancerous growth affecting the hematopoietic system (a "hematopoietic neoplasm"; e.g., lymphoma or leukemia). A neoplasm is an abnormal tissue growth, generally forming a distinct mass, that grows by cellular proliferation more rapidly than normal tissue growth. Neoplasms show partial or total lack of structural organization and functional coordination with normal tissue. As used herein, a "neoplasm", also referred to as a "tumor", is intended to encompass hematopoietic neoplasms as well as solid neoplasms. At least some of the cells of the neoplasm have a mutation in which the Ras gene (or an element of the Ras signaling pathway) is activated, either directly (e.g., by an activating mutation in Ras) or indirectly (e.g., by activation of an upstream element in the Ras pathway). Activation of an upstream element in the Ras pathway includes, for example, transformation with epidermal growth factor receptor (EGFR) or Sos. A neoplasm that results, at least in part, by the activation of Ras, an upstream element of Ras, or an element in the Ras signalling pathway is referred to herein as a "Ras-mediated neoplasm". One neoplasm that is particularly susceptible to treatment by the methods of the invention is pancreatic cancer, because of the prevalence of Ras-mediated neoplasms associated with pancreatic cancer. Other neoplasms that are Particularly susceptible to treatment by the methods of the invention include breast cancer, brain cancer (e.g., glioblastoma), lung cancer, prostate cancer, colorectal cancer, thyroid cancer, renal cancer, adrenal cancer, liver cancer, and leukemia.

The reovirus is typically administered in a physiologically acceptable carrier or vehicle, such as phosphate-buffered saline, to the neoplasm.

"Administration to a neoplasm" indicates that the reovirus is administered in a manner so that it contacts the cells of the neoplasm (also referred to herein as "neoplastic cells"). The route by which the reovirus is administered, as well as the formulation, carrier or vehicle, will depend on the location as well as the type of the neoplasm. A wide variety of administration routes can be employed. For example, for a solid neoplasm that is accessible, the reovirus can be administered by injection directly to the neoplasm. For a hematopoietic neoplasm, for example, the reovirus can be administered intravenously or intravascularly. For neoplasms that are not easily accessible within the body, such as metastases or brain tumors, the reovirus is administered in a manner such that it can be transported systemically through the body of the mammal and thereby reach the neoplasm (e.g., intrathecally, intravenously or intramuscularly). Alternatively, the reovirus can be administered directly to a single solid neoplasm, where it then is carried systemically through the body to metastases. The reovirus can also be administered subcutaneously, intraperitoneally, topically (e.g., for melanoma), orally (e.g., for oral or esophageal neoplasm), rectally (e.g., for colorectal neoplasm), vaginally (e.g., for cervical or vaginal neoplasm), nasally or by inhalation spray (e.g., for lung neoplasm).

The reovirus is administered in an amount that is sufficient to treat the neoplasm (e.g., an "effective amount"). A neoplasm is "treated" when administration of reovirus to cells of the neoplasm effects oncolysis of the neoplastic cells, resulting in a reduction in size of the neoplasm, or in a complete elimination of the neoplasm. The reduction in size of the neoplasm, or elimination of the neoplasm, is generally caused by lysis of neoplastic cells ("oncolysis") by the reovirus. The effective amount will be determined on an individual basis and may be based, at least in part, on consideration of the type of reovirus; the individual's size, age, gender; and the size and other characteristics of the neoplasm. For example, for treatment of a human, approximately $10^3$ to $10^{12}$ plaque forming units (PFU) of reovirus can be used, depending on the type, size and number of tumors present. The reovirus can be administered in a single dose, or multiple doses (i.e., more than one dose). The multiple doses can be administered concurrently, or consecutively (e.g., over a period of days or weeks). The reovirus can also be administered to more than one neoplasm in the same individual.

The invention is further illustrated by the following Exemplification.

EXEMPLICATION

Materials and Methods

Cells and Virus

Parental NIH-3T3 cell lines along with NIH-3T3 cells transformed with a number of oncogenes were obtained from a variety of sources. Parental NIH-3T3 and NIH-3T3 cells transfected with the Harvey-ras (H-ras) and EJ-ras oncogenes were a generous gift of Dr. Douglas Faller (Boston University School of Medicine). NIH-3T3 cells along with their Sos-transformed counterparts (designated TNIH#5) were a generous gift of Dr. Michael Karin (University of Calif., San Diego). Dr. H.-J. Kung (Case Western Reserve University) kindly donated parental NIH-3T3 cells along with NIH-3T3 cells transfected with the v-erbB oncogene (designated THC-11). 2H1 cells, a derivative of the C3H 10T1/2 murine fibroblast line, containing the Harvey-ras gene under the transcriptional control of the mouse metallothionein-I promoter were obtained from Dr. Nobumichi Hozumi (Mount Sinai Hospital Research Institute). These 2H1 cells are conditional ras transformant that express the H-ras oncogene in the presence of 50 µM $ZnSO_4$. All cell lines were grown in Dulbecco's modified Eagle's medium (DMEM) containing 10% fetal bovine serum (FBS).

The Dearing strain of reovirus serotype 3 used in these studies was propagated in suspension cultures of L cells and purified according to Smith (Smith, R. E. et al., (1969) Virology, 39:791-800) with the exception that β-mercaptoethanol (β-ME) was omitted from the extraction buffer. Reovirus labelled with [$^{35}$S]methionine was grown and purified as described by McRae and Joklik (McRae, M. A. and Joklik, W. K., (1978) Virology, 89:578-593). The particle/PFU ratio for purified reovirus was typically 100/1.

Immunofluorescent Analysis of Reovirus Infection

For the immunofluorescent studies the NIH-3T3, TNIH#5, H-ras, EJ-ras, 2H1 (+/−$ZnSO_4$), and THC-11 cells were grown on coverslips, and infected with reovirus at a multiplicity of infection (MOI) of $^-$10 PFU cell or mock-infected by application of the carrier agent (phosphate-buffered saline, PBS) to the cells in an identical fashion as the administration of virus to the cells. At 48 hours postinfection, cells were fixed in an ethanol/acetic acid (20/1) mixture for 5 minutes, then rehydrated by sequential washes in 75%, 50% and 25% ethanol, followed by four washes with phosphate-buffered saline (PBS). The fixed and rehydrated cells were then exposed to the primary antibody (rabbit polyclonal anti-reovirus type 3 serum diluted 1/100 in PBS) [antiserum prepared by injection of rabbits with reovirus serotype 3 in Freund's complete adjuvant, and subsequent bleedings] for 2 hours at room temperature. Following three washes with PBS, the cells were exposed to the secondary antibody [goat anti-rabbit IgG (whole molecule)-fluorescein isothiocyanate conjugate (FITC) [Sigma ImmunoChemicals F-0382] diluted 1/100 in PBS containing 10% goat serum and 0.005% Evan's Blue] for 1 hour at room temperature. Finally, the fixed and treated cells were washed three more times with PBS and then once with double-distilled water, dried and mounted on slides in 90% glycerol containing 0.1% phenylenediamine, and viewed with a Zeiss Axiophot microscope on which Carl Zeiss camera was mounted (the magnification for all pictures was 200×).

Radiolabelling of Reovirus-Infected Cells and Preparation of Lysates

Confluent monolayers of NIH-3T3, TNIH#5, H-ras, EJ-ras, 2H1 (+/−$ZnSO_4$), and THC-11 cells were infected with reovirus (MOI $^-$10 PFU/cell). At 12 hours postinfection, the media was replaced with methionine-free DMEM containing 10% dialyzed FBS and 0.1 mCi/ml [$^{35}$S] methionine. After further incubation for 36 hours at 37° C., the cells were washed in phosphate-buffered saline (PBS) and lysed in the same buffer containing 1% Triton X-100, 0.5% sodium deoxycholate and 1 mM EDTA. The nuclei were then removed by low speed centrifugation and the supernatants were stored at −70° C. until use.

Preparation of Cytoplasmic Extracts for In Vitro Kinase Assays

Confluent monolayers of the various cell lines were grown on 96 well cell culture planes. At the appropriate time postinfection the media was aspirated off and the cells were lysed with a buffer containing 20 mM HEPES [pH 7.4], 120 mM KCl, 5 mM $MgCl_2$, 1 mM dithiothreitol, 0.5% Nonidet P-40, 2 µg/ml leupeptin, and 50 µg/ml aprotinin. The nuclei were then removed by low-speed centrifugation and the supernatants were stored at −70° C. until use.

Cytoplasmic extracts were normalized for protein concentrations before use by the Bio-Rad protein microassay method. Each in vitro kinase reaction contained 20 µl of cell extract, 7.5 µl of reaction buffer (20 mM HEPES [pH 7.4], 120 mM KCl, 5 mM $MgCl_2$, 1 mM dithiothreitol, and 10% glycerol) and 7.0 µl of ATP mixture (1.0 µCi[γ-$^{32}$P]ATP in 7 µl of reaction buffer), and was incubated for 30 minutes at 37° C. (Mundschau, L. J., and Faller, D. V., J. Biol. Chem., 267: 23092-23098 (1992)). Immediately after incubation the labelled extracts were either boiled in Laemmli SDS-sample buffer or were either precipitated with agarose-poly(I)poly (C) beads or immunoprecipitated with an anti-PKR antibody.

Agarose poly(I)poly(C) Precipitation

To each in vitro kinase reaction mixture, 30 µl of a 50% Ag poly(I)poly(C) Type 6 slurry (Pharmacia LKB Biotechnology) was added, and the mixture was incubated at 4° C. for 1 h. The Ag poly(I)poly(C) beads with the absorbed, labelled proteins were then washed four times with was buffer (20 mM HEPES [7.5 pH], 90 mM KCl, 0.1 mM EDTA, 2 mM dithiothreitol, 10% glycerol) at room temperature and mixed with 2×Laemmli SDS sample buffer. The beads were then boiled for 5 min, and the released proteins were analyzed by SDS-PAGE.

Polymerase Chain Reaction

Cells at various times postinfection were harvested and resuspended in ice cold TNE (10 mM Tris [pH 7.8], 150 mM NaCl, 1 mM EDTA) to which Nonidet P40 (NP-40) was then added to a final concentration of 1%. After 5 minutes, the nuclei were pelleted and RNA was extracted from the supematant using the phenol:chloroform procedure. Equal amounts of total cellular RNA from each sample were then subjected to RT-PCR (Wong, H., et at., (1994) *Anal. Biochem.*, 223:251-258) using random hexanucleotide primers (Pharmacia) and RTase (GIBCO-BRL) according to the manufacturer's protocol. The cDNA's from the RT-PCR step were then subjected to selective amplification of reovirus cDNA using appropriate primers that amplify a predicted 116 bp fragment. These primer sequences were derived from the s1 sequence determined previously (Nagata, L., et al., (1984) Nucleic Acids Res.. 12:8699-8710). The GAPDH primers of Wong, H., et at.. (1994) Anal. Biochem., 223:251-258 were used to amplify a predicted 306 bp GAPDH fragment which served as a PCR and gel loading control. Selective amplification of the si and GAPDH cDNA's was performed using Taq DNA polymerase (GIBCO-BRL) according to the manufactures' protocol using a Perkin Elmer Gene Amp PCR system 9600. PCR was carried out for 28 cycles with each consisting of a denaturing step for 30 seconds at 97° C., annealing step for 45 seconds at 55° C., and polymerization step for 60 seconds at 72° C. PCR products were analyzed by electrophoresis through an ethidium bromide-impregnated TAE-2% agarose gel and photographed under ultra-violet illumination with Polaroid 57 film.

Immunoprecipitation and SDS-PAGE Analysis

Immunoprecipitation of $^{35}$S-labelled reovirus-infected cell lysates with anti-reovirus serotype 3 serum was carried out as previously described (Lee, P. W. K. et al. (1981) *Virology*, 108:134-146). Immunoprecipitation of $^{32}$P-labelled cell lysates with an anti-PKR antibody (from Dr. Michael Mathews, Cold Spring Harbor) was similarly carried out. Immunoprecipitates were analyzed by discontinuous SDS-PAGE according to the protocol of Laemmli (Laemmli, U. K., (1970) *Nature*, 227.680-685).

Example 1

Activated Intermediates in the Ras Signalling Pathway Augment Reovirus Infection Efficiency It was previously shown that 3T3 cells and their derivatives lacking epidermal growth factor receptors (EGFR) are poorly infectible by reovirus, whereas the same cells transformed with either EGFR or v-erb B are highly susceptible as determined by cytopathic effects, viral protein synthesis, and virus output (Strong, J. E. et al., (1993) *Virology*, 197:405-411; Strong, J. E. and Lee, P. W. K., (1996) *J. Virol.*, 70:612-616).

To determine whether downstream mediators of the EGFR signal transduction pathway may be involved, a number of different NIH 3T3-derived, transformed with constitutively activated oncogene downstream of the EGFR, were assayed for relative susceptibility to reovirus infection. Of particular interest were intermediates in the ras signalling pathway (reviewed by Barbacid, M., *Annu. Rev. Biochem.*, 56:779-827 (1987); Cahill, M. A., et al., *Curr. Biol.*, 6:16-19 (1996). To investigate the Ras signalling pathway, NIH 3T3 parental cell lines and NIH 3T3 lines transfected with activated versions of Sos (Aronheim, A., et al., (1994) *Cell*, 78:949-961) or ras (Mundschau, L. J. and Faller, D. V., (1992) *J. Biol. Chem.*, 267:23092-23098) oncogenes were exposed to reovirus, and their capacity to promote viral protein synthesis was compared.

Detection of viral proteins was initially carried out using indirect immunofluorescent microscopy as described above. The results indicated that whereas the NIH 3T3 cells adopted a typically flattened, spread-out morphology with marked contact inhibition, the transformed cells all grew as spindle-shaped cells with much less contact inhibition. On comparing the uninfected parental cell lines with the various transformed cell lines, it was apparent that the morphology of the cells was quite distinct upon transformation. Upon challenge with reovirus, it became clear that parental NIH 3T3 line was poorly infectible (<5%), regardless of the source of the parental NIH 3T3 line. In contrast, the transfected cell lines each demonstrated relatively pronounced immunofluorescence by 48 hours postinfection (data not shown).

To demonstrate that viral protein synthesis was more efficient in the Sos- or Ras-transformed cell lines, cells were continuously labeled with [$^{35}$S]-methionine from 12 to 48 hr postinfection and the proteins were analyzed by sodium dodecyl sulfate-polyacrylamide gel electrophoresis (SDS-PAGE), as described above.

The results showed clearly that the levels of viral protein synthesis were significantly higher in the Sos- or Ras-transformed cells than in parental NIH 3T3 cells. The identities of the viral bands were confirmed by immunoprecipitation of the labeled proteins with polyclonal anti-reovirus antibodies. Since the uninfected NIH 3T3 cells and their transformed counterparts displayed comparable levels of cellular protein synthesis and doubling times (data not shown), the observed difference in the level of viral protein synthesis could not be due to intrinsic differences in growth rates or translation efficiencies for these cell lines.

Example 2

Enhanced Infectibility Conferred by Activated Oncogenes is not Due to Long-Term Transformation To determine whether the differences in susceptibility may be the result of long-term effects of transformation, or the result of the activated oncogene itself, a cell line expressing a zinc-inducible cellular Harvey-ras (c-H-ras) gene was tested for susceptibility to reovirus infectibility, as described above. These cells, called 2H1, were derived from the C3H 10T1/2 cell line which is poorly infectible by reovirus (data not shown), and carry the c-H-ras gene under the control of the mouse metallothionine-I promoter (Trimble, W. S. et al. (1986) *Nature*, 321:782-784).

Cells were either mock-treated or pretreated with 50 µM ZnSO$_4$ 18 hours prior to infection or mock-infection (administration of carrier agent), followed by indirect immunofluorescent analysis of these cells at 48 hours postinfection or mock-infection.

The results (not shown) demonstrated that uninduced cells were poorly infectible (<8%) whereas those induced for only 18 hours were much more susceptible (>40%). Enhanced viral protein synthesis in the Zn-induced 2H1 cells was further confirmed by metabolic labeling of the cells with [$^{35}$S] methionine followed by SDS-PAGE analysis of virus-specific proteins (not shown).

Based on these observations, the augmentation of reovirus infection efficiency in the transformed cells is a direct result of the activated oncogene product(s), and not due to other factors such as aneuploidy often associated with long-term transformation, or other accumulated mutations that may be acquired under a chronically transformed state (e.g., p53 or myc activation).

Example 3

Viral Transcripts are Generated but not Translated in Reovirus-Resistant NIH 3T3 Cells The step at which reovirus infection is blocked in nonsusceptible NIH 3T3 cells was also identified. Because virus binding and virus internalization for nonsusceptible cells were comparable to those observed for susceptible cells (Strong, J. E. et al., (1993) *Virology*, 197:405-411), the transcription of viral genes was investigated.

The relative amounts of reovirus S1 transcripts generated in NIH 3T3 cells and the Ras-transformed cells during the first 12 hours of infection were compared after amplification of these transcripts by polymerase chain reaction (PCR), as described above. The results demonstrated that the rates of accumulation of S1 transcripts in the two cell lines were similar, at least up to 12 hours postinfection. Similar data were obtained when rates of accumulation of other reovirus transcripts were compared (data not shown). These results demonstrate that infection block in nonsusceptible cells is not at the level of transcription of viral genes, but rather, at the level of translation of the transcripts.

Example 4

A 65 kDa Protein is Phosphorylated in Reovirus-Treated NIH 3T3 Cells but not in Reovirus-Infected Transformed Cells Because viral transcripts were generated, but not translated, in NIH 3T3 cells, it was investigated whether the double-stranded RNA (dsRNA)-activated kinase, PKR, is activated (phosphorylated) in these cells (for example, by S1 mRNA transcripts which have been shown to be potent activators of PKR ((Bischoff, J. R. and Samuel, C. E., (1989) *Virology*, 172:106-115), which in turn leads to inhibition of translation of viral genes. The corollary of such a scenario would be that in the case of the transformed cells, this activation is prevented, allowing viral protein synthesis to ensue.

NIH 3T3 cells and v-erbB- or Ras-transformed cells (designated THC-11 and H-ras, respectively) were treated with reovirus (i.e., infected) or mock-infected (as above), and at 48 hours post treatment, subjected to in vitro kinase reactions, followed by autoradiographic analysis as described above.

The results clearly demonstrated that there was a distinct phosphoprotein migrating at approximately 65 kDa, the expected size of PKR, only in the NIH 3T3 cells and only after exposure to reovirus. This protein was not labeled in the lysates of either the uninfected transformed cell lines or the infected transformed cell lines. Instead, a protein migrating at approximately 100 kDa was found to be labeled in the transformed cell lines after viral infection. This protein was absent in either the preinfection or the postinfection lysates of the NIH 3T3 cell line, and was not a reovirus protein because it did not react with an anti-reovirus serum that precipitated all reovirus proteins (data not shown). A similar 100 kDa protein was also found to be $^{32}$P-labeled in in vitro kinase reactions of postinfection lysates of the Sos-transformed cell lines (data not shown).

That intermediates in the Ras signalling pathway were responsible for the lack of phosphorylation of the 65 kDa protein was further confirmed by the use of the 2H1 cells which contain a Zn-inducible Ras oncogene. Uninduced 2H1 cells (relatively resistant to reovirus infection, as shown above), were capable of producing the 65 kDa phosphoprotein only after exposure to virus. However, 2H1 cells subjected to Zn-induction of the H-Ras oncogene showed significant impairment of the production of this phosphoprotein. This impairment coincided with the enhancement of viral synthesis. These results therefore eliminated the possibility that the induction of the 65 kDa phosphoprotein was an NIH 3T3-specific event, and clearly established the role of Ras in preventing (or reversing) induction of the production of this phosphoprotein. The Zn-induced 2H1 cells did not produce the 100 kDa phosphoprotein seen in the infected, chronically transformed H-Ras cells.

Example 5

Induction of Phosphorylation of the 65 kDa Protein Requires Active Viral Transcription Since production of the 65 kDa phosphoprotein occurred only in cells that were resistant to reovirus infection, and only after the cells were exposed to reovirus, it was investigated whether active viral transcription was required for production of the 68 kDa phosphoprotein. Reovirus was UV-treated to inactivate its genome prior to administration of the reovirus to NIH 3T3 cells. For UV-treatment, reovirus was suspended in DMEM to a concentration of approximately $4 \times 10^6$ PFU/mL and exposed to short-wave (254 nm) UV light for 20 minutes. UV-inactivated virus were non-infectious as determined by lack of cytopathic effects on mouse L-929 fibroblasts and lack of viral protein synthesis by methods of [$^{35}$S]-methionine labelling as previously described. Such UV treatment abolished viral gene transcription, as analyzed by PCR, and hence viral infectivity (data not shown). The cells were then incubated for 48 hours, and lysates were prepared and subjected to in vitro $^{32}$P-labeling as before. The results showed that NIH 3T3 cells infected with untreated reovirus produced a prominent 65 kDa $^{32}$P-labelled band not found in uninfected cells. Cells exposed to UV-treated reovirus behaved similarly to the uninfected control cells, manifesting little phosphorylation of the 65 kDa protein. Thus, induction of the phosphorylation of the 65 kDa phosphoprotein is not due to dsRNA present in the input reovirus; rather, it requires de novo transcription of the viral genes, consistent with the identification of the 65 kDa phosphoprotein as PKR.

Example 6

Identification of the 65 kDa Phosphoprotein as PKR

To determine whether the 65 kDa phosphoprotein was PKR, a dsRNA binding experiment was carried out in which poly(I)-poly(c) agarose beads were added to $^{32}$P-labeled lysates, as described above. After incubation for 30 minutes at 4° C., the beads were washed, and bound proteins were released and analyzed by SDS-PAGE. The results showed that the 65 kDa phosphoprotein produced in the postinfection NIH 3T3 cell lysates was capable of binding to dsRNA; such binding is a well-recognized characteristic of PKR. In contrast, the 100 kDa phosphoprotein detected in the infected H-ras-transformed cell line did not bind to the Poly(I)-poly(c) agarose. The 65 kDa phosphoprotein was also immunoprecipitable with a PKR-specific antibody (provided by Dr. Mike Mathews, Cold Spring Harbor Laboratory), confirming that it was indeed PKR.

Example 7

2-aminopurine Treatment of NIH 3T3 Cells Confers Enhanced Infectibility

If PKR phosphorylation is responsible for the shut-off of viral gene translation in NIH-3T3 cells, and one of the functions of the activated oncogene product(s) in the transformed cells is the prevention of this phosphorylation event, then inhibition of PKR phosphorylation in NIH-3T3 cells by other means (e.g. drugs) should result in the enhancement of viral protein synthesis, and hence infection, in these cells. To test this idea, 2-aminopurine was used. This drug has been shown to possess relatively specific inhibitory activity towards PKR autophosphorylation (Samuel, C. E. and Brody, M., (1990) Virology, 176:106-113; Hu, Y. and Conway, T. W. (1993), J. Interferon Res., 13:323-328). Accordingly, NIH 2T3 cells were exposed to 5 nM 2-aminopurine concurrently with exposure to reovirus. The cells were labeled with [$^{35}$S]methionine from 12 to 48 h postinfection, and lysates were harvested and analyzed by SDS-PAGE.

The results demonstrated that exposure to 2-aminopurine resulted in a significantly higher level of viral protein synthesis in NIH 3T3 cells (not shown). The enhancement was particularly pronounced after immunoprecipitating the lysates with an anti-reovirus serum. These results demonstrate that PKR phosphorylation leads to inhibition of viral gene translation, and that inhibition of this phosphorylation event releases the translation block. Therefore, intermediates in the Ras signalling pathway negatively regulate PKR, leading to enhanced infectibility of Ras-transformed cells.

Interferon β, known to induce PKR expression, was found to significantly reduce reovirus replication in Ras-transformed cells date not shown).

Example 8

In Vivo Oncolytic Capability of Reovirus

A severe combined immunodeficiency (SCID) host tumor model was used to assess the efficacy of utilizing reovirus for tumor reduction. Male and female SCID mice (Charles River, Canada) were injected with v-erbB-transformed NIH 3T3 mouse fibroblasts (designated THC-11 cells) in two subcutaneous sites overlying the hind flanks. In a first trial, an injection bolus of $2.3 \times 10^5$ cells in 100 μl of sterile PBS was used. In a second trial, an injection bolus of $4.8 \times 10^6$ cells in 100 μl PBS was used. Palpable tumors were evident approximately two to three weeks post injection.

Reovirus serotype three (strain Dearing) was injected into the right-side tumor mass (the "treated tumor mass") in a volume of 20 μl at a concentration of $1.0 \times 10^9$ plaque forming units (PFU)/ml. The left-side tumor mass (the "untreated tumor mass") was left untreated. The mice were observed for a period of seven days following injection with reovirus, measurements of tumor size were taken every two days using calipers, and weight of tumors was measured after sacrifice of the animals. All mice were sacrificed on the seventh day. Results are shown in Table 1.

TABLE 1

Tumor Mass after Treatment with Reovirus

| Trial 1 (n = 8) | mean untreated tumor mass | 602 mg |
|---|---|---|
|  | mean treated tumor mass | 284 mg |
| Trial 2 (n = 12) | mean control tumor mass | 1523.5 mg |
|  | mean untreated tumor mass | 720.9 mg |
|  | mean treated tumor mass | 228.0 mg |

The treated tumor mass was 47% of that of the untreated tumor mass in trial 1, and 31.6% of the untreated tumor mass in trial 2. These results indicated that the virus-treated tumors were substantially smaller than the untreated tumors, and that there may be an additional systemic effect of the virus on the untreated tumor mass.

Example 9

In Vivo Oncolytic Capability of Reovirus Against Human Breast Cancer-Derived Cell Lines In vivo studies were also carried out using human breast carcinoma cells in a SCID mouse model. Female SCID mice were injected with $1 \times 10^6$ MDAMB468 cells in two subcutaneous sites, overlying both hind flanks. Palpable tumors were evident approximately two to four weeks post injection. Undiluted reovirus serotype three (strain Dearing) was injected into the right side tumor mass in a volume of 20 μl at a concentration of $1.0 \times 10^{10}$ PFU/ml. The following results were obtained:

TABLE 2

Tumor Mass After Treatment with Reovirus

| TREATMENT | mean untreated tumor mass (left side) | mean treated tumor mass (right side) |
|---|---|---|
| Reovirus (N = 8) | 29.02 g | 38.33 g |
| Control (N = 8) | 171.8 g | 128.54 g |

*Note:
One of the control mice died early during the treatment phase. None of the reovirus-treated mice died.

Although these studies were preliminary, it was clear that the size of the tumors in the reovirus-treated animals was substantially lower than that in the untreated animals. However, the size of the tumors on the right (treated) side of the reovirus-treated animals was slightly larger on average than the left (untreated) side. This was unexpected but may be explained by the composition of the mass being taken up by inflammatory cells with subsequent fibrosis, as well as by the fact that these tumors were originally larger on the right side on average than the left. The histologic composition of the tumor masses is being investigated. These results also support the systemic effect the reovirus has on the size of the untreated tumor on the contralateral slide of reovirus injection.

Example 10

Susceptibility of Additional Human Tumors to Reovirus Oncolysis

In view of the in vivo results presented above, the oncolytic capability observed in murine cells was investigated in cell lines derived from additional human tumors.

A. Materials and Methods

Cells and Virus

All cell lines were grown in Dulbecco's modified Eagle's medium (DMEM) containing 10% fetal bovine serum (FBS). The Dearing strain of reovirus serotype 3 used in these studies was propagated in suspension cultures of L cells and purified according to Smith (Smith, R. E. et al., (1969) *Virology*, 39:791-800) with the exception that β-mercaptoethanol (β-ME) was omitted from the extraction buffer. Reovirus labelled with [$^{35}$S]methionine was grown and purified as described by McRae and Joklik (McRae, M. A. and Joklik, W. K., (1978) *Virology*, 89:578-593). The particle/PFU ration for purified reovirus was typically 100/1.

Cytopathic Effects of Reovirus on Cells

Confluent monolayers of cells were infected with reovirus serotype 3 (strain Dearing) at a multiplicity of infection (MOI) of approximately 40 plaque forming units (PFU) per cell. Pictures were taken at 36 hour postinfection for both reovirus-infected and mock-infected cells.

Immunofluorescent Analysis of Reovirus Infection

For the immunofluorescent studies the cells were grown on coverslips, and infected with reovirus at a multiplicity of infection (MOI) of ~10 PFU/cell or mock-infected as described above. At various times postinfection, cells were fixed in an ethanol/acetic acid (20/1) mixture for 5 minutes, then rehydrated by subsequential washes in 75%, 50% and 25% ethanol, followed by 4 washes with phosphate-buffered saline (PBS). The fixed and rehydrated calls were then exposed to the primary antibody (rabbit polyclonal anti-reovirus type 3 serum diluted 1/100 in PBS) for 2 hr at room temperature. Following 3 washes with PBS, the cells were exposed to the secondary antibody [goat anti-rabbit IgG (whole molecule) fluorescein isothiocyanate (FITC) conjugate diluted 1/100 in PBS containing 10% goat serum and 0.005% Evan's Blue counterstain] for 1 hour at room temperature. Finally, the fixed and treated cells were washed 3 more times with PBS, followed by 1 wash with double-distilled water, dried and mounted on slides in 90% glycerol containing 0.1% phenylenediamine, and viewed with a Zeiss Axiophot microscope mounted with a Carl Zeiss camera (magnification for all pictures was 200×).

Infection of Cells and Quantitation of Virus

Confluent monolayers of cells grown in 24-well plates were infected with reovirus at an estimated multiplicity of 10 PFU/cell. After 1 hour incubation at 37° C., the monolayers were washed with warm DMEM-10% FBS, and then incubated in the same medium. As various times postinfection, a mixture of NP-40 and sodium deoxycholate was added directly to the medium on the infected monolayers to final concentrations of 1% and 0.5%, respectively. The lysates were then harvested ard virus yields were determined by plaque titration on L-929 cells.

Radiolabelling of Reovirus-Infected Cells and Preparation of Lysates

Confluent monolayers of cells were infected with reovirus (MOI ~10 PFU/cell). At various times postinfection, the media was replaced with methionine-free DMEM containing 10% dialyzed PBS and 0.1 mCi/ml [$^{35}$S] methionine. After further incubation for 1 hour at 37° C., the cells were washed in phosphate-buffered saline (PBS) and lysed in the same buffer containing 1% Triton X-100, 0.5% sodium deoxycholate and 1 mM EDTA. The nuclei were then removed by low speed centrifugation and the supernatants was stored at 70° C. until use.

Immunoprecipitation and SDS-PAGE Analysis

Immunoprecipitation of [$^{35}$S]-labelled reovirus-infected cell lysates with anti-reovirus serotype 3 serum was carried out as previously described (Lee, P. W. K. et al. (1981) *Virology*, 108:134-146). Immunoprecipitates were analyzed by discontinuous SDS-PAGE according to the protocol of Laemmli (Laemmli, U. K., (1970) *Nature*, 227:680-685).

B. Breast Cancer

The c-erbB-2/neu gene encodes a transmembrane protein with extensive homology to the EGFR that is overexpressed in 20-30% of patients with breast cancer (Yu, D. et al. (1996) *Oncogene* 13:1359). Since it has been established herein that Ras activation, either through point mutations or through augmented signaling cascade elements upstream of Ras (including the c-erbB-2/neu homologue EGFR) ultimately creates a hospitable environment for reovirus replication, an array of cell lines derived from human breast cancers were assayed for reovirus susceptibility. The cell lines included MDA-MD-435SD (ATCC deposit HTB-129), MCF-7 (ATCC deposit HTB-22), T-27-D (ATCC deposit HTB-133), BT-20 (ATCC deposit HTB-19), HBL-100 (ATCC deposit HTB-124), MDA-MB-463 (ATCC deposit HTB-132), and SKBR-3 (ATCC deposit HTB-30.

Based upon induction of cytopathic effects, and viral protein synthesis as measured by radioactive metabolic labeling and immunofluorescence as described above, it was found that five out of seven of the tested breast cancers were susceptible to reovirus infection: MDA-MB-435S, MCF-7, T-27-D, MDA MB-468, and SKBR-3 were exquisitely sensitive to infection, while BT-20 and HBL-100 demonstrated no infectibility.

C. Brain Glioblastoma

Next a variety of cell lines derived from human brain glioblastomas was investigated. The cell lines included A-172, U-118, U-178, U-563, U-251, U-87 and U-373 (cells were a generous gift from Dr. Wee Yong, University of Calgary).

Six out of seven glioblastoma cell lines demonstrated susceptibility to reovirus infection, including U-118, U-178, U-563, U-251, U-87 and U-373, while A-172 did not demonstrate any infectibility, as measured by cytopathic effects, immunofluorescence and [$^{35}$S]-methionine labeling of reovirus proteins.

D. Pancreatic Carcinoma

Cell lines derived from pancreatic cancer were investigated for their susceptibility to reovirus infection. The cell lines included Capan-1 (ATCC deposit HTB-79), BxPC3 (ATCC deposit CRL-1687), MIAPACA-2 (ATCC deposit CRL-1420), PANC-1 (ATCC deposit CRL-1469), AsPC-1 (ATCC deposit CRL-1682) and Hs766T (ATCC deposit HTB-134).

Five of these six cell lines demonstrated susceptibility to reovirus infection including Capan-1, MIAPACA-2, PANC-1, AsPC-1 and Hs766T, whereas BxPC3 demonstrated little infectability as assayed by virus-induced cytopathological effects, immunofluorescence and [$^{35}$S]-labelling. Interestingly, four of the five cell lines demonstrating susceptibility to reovirus oncolysis have been shown to possess transforming mutations in codon 12 of the K-ras gene (Capan-1, MIAPACA-2, PANC-1 and AsPC-1) whereas the one lacking such susceptibility (BxPC3) has been shown to lack such a mutation (Berrozpe, G., et al. (1994), *Int. J. Cancer*, 58:185-191). The status of the other K-ras codons is currently unknown for the Hs766T cell line.

Equivalents

Those skilled in the art will be able to recognize, or be able to ascertain, using no more than routine experimentation, many equivalents to the specific embodiments of the invention described herein. Such equivalents are intended to be encompassed by the following claims.

What is claimed is:

1. A method of treating a Ras-mediated neoplasm in a mammal that has been previously exposed to a reovirus, comprising administering to the neoplasm a reovirus in an amount sufficient to result in reovirus-mediated oncolysis of cells of the neoplasm.

2. The method of claim 1, wherein the reovirus is a human reovirus.

3. The method of claim 1, wherein more than one type of reovirus is administred.

4. The method of claim 1, wherein more than one strain of the reovirus is administered.

5. The method of claim 1, wherein the reovirus is a field isolate.

6. The method of claim 1, wherein the reovirus is treated with a protease prior to administration.

7. The method of claim 1, wherein the neoplasm is a solid neoplasm.

8. The method of claim 1, wherein the reovirus is administered by a route selected from the group consisting of intravenous, intravascular, intrathecal, intramuscular, subcutaneous, intraperitoneal, topical, oral, rectal, viginal and nasal administration.

9. The method of claim 1, wherein the mammal is selected from the group consisting of: mice, dog, cats, sheep, goats, cows, horses, pigs, and non-human primates.

10. The method of claim 1, wherein the mammal is a human.

11. The method of claim 1, wherein the neoplasm is selected from the group consisting of: lung cancer, prostate cancer, colorectal cancer, thyroid cancer, renal cancer, adrenal cancer, liver cancer, pancreatic cancer, breast cancer, brain cancer and leukemia.

12. The method of claim 1, wherein approximately $10^3$ to $10^{12}$ plaque forming units of the reovirus are administered.

13. The method of claim 1, wherein the reovirus is administred in a single dose.

14. The method of claim 1, wherein the ras-mediated neoplasm is metastatic.

15. The method of claim 2, wherein the reovirus is selected from the group consisting of type 1 reovirus, type 2 reovirus and type 3 reovirus.

16. The method of claim 7, wherein the reovirus is administered by injection into the solid neoplasm.

17. The method of claim 7, wherein the revirus is administered intravenously into the mammal.

18. A pharmaceutical compostion for treating a Ras-mediated neoplasm in a mammal, comprising:
   (i) a pharmaceutically effective amount of approximately $10^3$ to $10^4$ plaque forming units of reovirus or $10^{10}$ to $10^{12}$ plaque forming units of a reovirus; and
   (ii) a physiologically acceptable carrier.

19. The pharmaceutical composition of claim 18 wherein said pharmaceutically effective amount is approximately $10^{10}$ to $10^{12}$ plaque forming units of reovirus.

20. The pharmaceutical composition for treating a Ras-mediated neoplasm in a mammal, comprising:
   (i) a pharmaceutically effective amount of a chemically or biochemically pre-treated reovirus; and
   (ii) a physiologically acceptable carrier.

21. The pharmaceutical composition of claim 20 wherein the pharmaceutically effective amount is approximately $10^3$ to $10^{12}$ plaque forming units of reovirus.

22. A pharmaceutical composition for treating a Ras-mediated neoplasm in a mammal, comprising:
   (i) a pharmaceutically effective amount of a non-human mammalian reovirus or a non-mammalian reovirus; and
   (ii) a physiologically acceptable carrier.

23. The pharmaceutical composition of claim 22 wherein the pharmaceutically effective amount is approximately $10^3$ to $10^{12}$ plaque forming units of reovirus.

* * * * *

UNITED STATES PATENT AND TRADEMARK OFFICE
CERTIFICATE OF CORRECTION

PATENT NO.         : 7,476,382 B2
APPLICATION NO.    : 10/836857
DATED              : January 13, 2009
INVENTOR(S)        : Patrick W. K. Lee It is certified that error appears in the above-identified patent and that said Letters Patent is hereby corrected as shown below:

On the first page, column 2, under "Other Publications," line 24, insert before "Virol" --of--

At column 15, line 10, "administred" should read --administered--

At column 15, line 22, "viginal" should read --vaginal--

At column 15, line 25, "dog" should read --dogs--

At column 15, lines 36-37, "administred" should read --administered--

At column 16, line 8, "revirus" should read --reovirus--

At column 16, line 10, "compostion" should read --composition--

At column 16, line 19, delete "The" and insert --A-- therefor

Signed and Sealed this

Fourteenth Day of April, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,476,382 B2  Page 1 of 1
APPLICATION NO. : 10/836857
DATED : January 13, 2009
INVENTOR(S) : Lee et al.

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (471) days Delete the phrase "by 471 days" and insert -- by 415 days --

Signed and Sealed this

Thirteenth Day of October, 2009

David J. Kappos
*Director of the United States Patent and Trademark Office*

UNITED STATES PATENT AND TRADEMARK OFFICE
CERTIFICATE OF CORRECTION

PATENT NO. : 7,476,382 B2  Page 1 of 1
APPLICATION NO. : 10/836857
DATED : January 13, 2009
INVENTOR(S) : Lee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 859 days.

Signed and Sealed this
First Day of March, 2011

David J. Kappos
*Director of the United States Patent and Trademark Office*